(12) United States Patent
Mittenzwey et al.

(10) Patent No.: US 8,355,121 B2
(45) Date of Patent: Jan. 15, 2013

(54) DEVICE FOR MEASURING THE DIFFUSION AND/OR ABSORPTION AND/OR REFRACTION OF A SAMPLE

(75) Inventors: Klaus-Henrik Mittenzwey, Berlin (DE); Gert Sinn, Berlin (DE)

(73) Assignee: KROHNE Optosens, Neuss (DE)

( * ) Notice: Subject to any disclaimer, the term of this patent is extended or adjusted under 35 U.S.C. 154(b) by 671 days.

(21) Appl. No.: 12/418,333

(22) Filed: Apr. 3, 2009

(65) Prior Publication Data

US 2009/0251688 A1  Oct. 8, 2009

(30) Foreign Application Priority Data

Apr. 3, 2008 (DE) .......................... 10 2008 017 433

(51) Int. Cl.
*G01N 21/00* (2006.01)
(52) U.S. Cl. ........................................................ 356/73
(58) Field of Classification Search .............. 356/72–73, 356/445–446, 432
See application file for complete search history.

(56) References Cited

U.S. PATENT DOCUMENTS 6,118,520 A * 9/2000 Harner ............................. 356/73
7,271,883 B2 * 9/2007 Newell et al. .................... 356/73

FOREIGN PATENT DOCUMENTS

| DE | 199 20 184 A1 | 11/2000 |
| DE | 199 34 934 C1 | 6/2001 |
| DE | 100 02 238 A1 | 7/2001 |
| DE | 100 59 920 A1 | 6/2002 |
| DE | 101 18 671 A1 * | 10/2002 |
| DE | 10 2004 018 754 A1 | 11/2005 |

OTHER PUBLICATIONS

English translation of DE 101 18 671 A1 Sep. 12, 2011.*

* cited by examiner

*Primary Examiner* — Kara E Geisel
(74) *Attorney, Agent, or Firm* — Roberts Mlotkowski Safran & Cole, P.C.; David S. Safran

(57) ABSTRACT

Device for measuring at least one of diffusion, absorption and refraction of a sample, having a radiation source, at least one receiving element, an optical imaging element and a protection element, the radiation source and the receiving element being arranged on the sensor side of the optical imaging element, the protection element being arranged on the sample side of the imaging element and adjacent to the imaging element and the radiation source. A refraction radiation source and a refraction receiver are arranged on the sensor side of the imaging element and arranged relative to the imaging element so that the refraction radiation of the sample specularly reflected by the sample side interface of the protection element can essentially be received by the refraction receiver and the radiation specularly reflected by the imaging element side interface of the protection element essentially cannot be received by the refraction receiver.

18 Claims, 2 Drawing Sheets

DEVICE FOR MEASURING THE DIFFUSION AND/OR ABSORPTION AND/OR REFRACTION OF A SAMPLE

BACKGROUND OF THE INVENTION

1. Field of Invention

The invention relates to a device for measuring the diffusion and/or absorption and/or refraction of a sample, having a radiation source, at least one receiving element, an optical imaging element and a protection element, wherein the radiation source and the receiving element are arranged on the sensor side of the optical imaging element, wherein the protection element is arranged on the sample side of the imaging element and adjacent to the imaging element, and wherein the radiation source, the imaging element and the receiving element are collectively arranged so that directly transmitted and/or specularly reflected sample radiation can be received by the receiving element.

2. Description of Related Art

Measuring devices of the type mentioned above have been known for quite some time and are used in the fields of chemical analysis and environmental, quality and process control. Such devices are known as encapsulated measuring probes, which are introduced into the control process. In the same manner, such a device can be applied in the context of a large measuring device that, for example, has a sample area for holding the sample to be tested.

A device for detecting diffuse and specular reflection in essentially non-transparent samples is known, for example, from German Patent Application DE 199 20 184 A1 and a device for measuring the diffusion and absorption of samples is known from German Patent Application DE 10 2004 018 754 A1, wherein, here, the major aspect is the examination of essentially transparent samples. At any rate, the devices are similar in that the radiation emitted by the radiation source divergently falls on the imaging element, for example, a lens, and is collimated by the imaging element to a parallel bundle of rays. This parallel radiation strikes the sample, which can be solid, liquid or also gaseous. In the case of transparent sample, the radiation passes through the sample and is reflected by a mirror back to the imaging element, i.e., the radiation passes through the sample twice. In the case of non-transparent samples, the emitted radiation is either specularly reflected or diffusely remitted by the sample and, thus, passes back through the imaging element in the direction of the receiving element.

The radiation source, the imaging element and the receiving element are collectively arranged so that directly transmitted and/or specularly reflected sample radiation can be received by the receiving element. However, the receiving element in the measuring device known from the prior art is not only struck by the transmitted and/or specularly reflected sample radiation, but also by diffusion radiation emanating essentially non-directionally from the sample.

In order to be able to distinguish between the diffusion radiation received by the receiving element and the transmitted and/or specularly reflected sample radiation received by the receiving element, an additional diffusion radiation receiving element is provided, which is collectively arranged in the measuring device so that it essentially can only be struck by diffusion radiation, but cannot be struck by the transmitted and/or specularly reflected sample radiation. Thus, the amount of transmitted and/or specularly reflected sample radiation can be determined from the total radiation determined by the receiving element allowing for the diffusion radiation determined by the diffusion radiation receiving element.

If the transmitted and the specularly reflected sample radiation is to be simultaneously and distinguishably receivable and determinable by the known device, then, not only is one single receiving element necessary, but also an additional receiving element, wherein care should be taken that each of the receiving elements either can only be struck essentially by the transmitted or essentially by the specularly reflected sample radiation, wherein—as is given in the above description—both receiving elements can be struck additionally by diffusion radiation. In the known devices, the radiation source and the receiving element are arranged in a radiation and receiving plane, which runs perpendicular to the optical axis of the imaging element and is essentially located at a distance from the imaging element as is allowed by the focal length. Under this condition, a focused image of the radiation source can be created by the receiving element, or respectively, the receiving elements, which is why radiation running along different optical paths is easily separated from one another in terms of imaging.

However, it has been pointed out that, in practice, in the use of protection elements that are arranged on the sample side of the imaging element and that normally form a transparent separating layer between the sensor part of the device and the sample part of the device, inaccuracies occur while detecting the diffusion and/or absorption and/or refraction of a sample.

SUMMARY OF THE INVENTION

A primary object of the present invention is, thus, to provide a device in which the measuring inaccuracies in the known device for measuring of diffusion and/or absorption and/or refraction of a sample are—at least partially—avoided. According to the invention, it has been determined that different disadvantageous effects occur while detecting signals for the refraction of the sample—i.e., signals caused by specularly reflected sample radiation—with a receiver that is arranged, in particular, in the radiation and receiving plane.

On the one hand, it has been determined that it is not possible to strictly separate the specular reflexes that, on the one hand, are specularly reflected by the imaging element side interface of the protection element, and on the other hand, are specularly reflected by the sample side interface of the protection window, wherein the last-mentioned reflexes characterize the refraction of the sample. The overlapping of these reflexes caused by both interfaces of the protection element ranges differs in strength depending on whether or not the imaging element side interface has an antireflective coating or not.

On the other hand, it has been determined that the known devices are disadvantageous in the measuring of transparent samples with a mirror to the effect that the transmitted radiation is directed to the same area in which the specular reflexes of the sample side interface of the protection element are found. Thus, the transmitted radiation overlaps the target signal of the specular reflection in an interfering manner.

The above object is, firstly and essentially, met according to the invention with the device discussed here in that a refraction radiation source and a refraction receiver are arranged on the sensor side of the imaging element and arranged in regard to the imaging element so that the refraction radiation of the sample specularly reflected by the sample side interface of the protection element can essentially be received by the refraction receiver and the radiation specularly reflected by the imaging element side interface of the protection element essentially cannot be received by the refraction receiver. The arrangement of the refraction radiation source and the refraction receiver according to the invention ensures that refraction radiation of interest of the sample specularly reflected by the sample side interface of the protection element is not overlapped by the radiation specularly reflected by the imaging element side interface of the protection element, so that the refraction radiation of the sample can be selectively determined. When speaking of a "refraction radiation source" and a "refraction receiver," then, in this context it is meant that this radiation source and the receiver assigned to this radiation source are intended to determine the refraction radiation of the sample, however, it does not mean that the refraction radiation source or the refraction receiver itself are based on the effect of refraction or that this effect has a decisive meaning for the refraction radiation source or the refraction receiver itself.

In a preferred embodiment of the invention, the distance of the refraction radiation source from the optical axis of the imaging element is larger than the distance of the radiation source from the optical axis of the imaging element, wherein it is particularly preferred that the distance of the refraction receiver from the optical axis of the imaging element be larger than the distance of the receiving element from the optical axis of the imaging element. By implementing this measure, in particular, transmitted radiation does not overlap the target signal of the specularly reflected refraction radiation of the sample. The radiation path of the radiation emitted by the refraction radiation source and received by the refraction receiver, sort-of, goes around the radiation path of the transmitted sample radiation emitted by the radiation source and received by the receiving element.

According to a further embodiment of the invention, the refraction radiation source is arranged between the radiation source and the imaging element, and additionally or alternatively, the refraction receiver is arranged further away from the imaging element than the receiving element. This measure greatly improves the signal-to-noise ratio of specularly reflected refraction radiation and diffusion radiation on the refraction receiver since the undirected diffusion radiation diminishes with the square of the distance from its origin; however, the directed refraction radiation is not subject to this square law.

In a further preferred embodiment of the invention, the refraction radiation source emits radiation at at least one defined wavelength, wherein the refraction receiver has, in particular, a specific sensitivity to the radiation of the refraction radiation source, which, for example, can be implemented using a corresponding optical filter. This embodiment guarantees that the refraction receiver receives significantly only the refraction radiation of the sample emitted by the refraction radiation source and specularly reflected by the sample side interface of the protection element, which leads to a further improvement of the signal-to-noise ratio.

In a further advantageous embodiment of the invention, a diffusion receiver is provided and arranged so that the diffusion receiver can essentially be struck by the diffusion radiation of the sample and the diffusion receiver, in particular and essentially, cannot be struck by the specularly reflected refraction radiation of the sample. In this context, it is provided by a particularly preferred embodiment of the invention that the device is arranged so that the diffusion radiation received from the diffusion receiver and identified can be used to compensate the diffusion radiation, which can be received by the refraction receiver. This occurs, in particular, by subtracting a weighted portion of the diffusion radiation received and identified by the diffusion receiver from the radiation received and identified by the refraction receiver, wherein it is a matter of the total radiation here, which also encompasses the diffusion radiation. The "weighted" portion of the diffusion radiation received and identified by the diffusion receiver means that the radiation identified by the receiver and diffusion receiver and the corresponding output signal have to be coordinated, wherein, e.g., different receiving areas, different reinforcements and different positions of both receivers have to be allowed for.

In a particularly advantageous embodiment of the invention, at least one diffusion receiver is arranged on the sensor side of and adjacent to the imaging element, wherein the diffusion receiver is directed toward the sample and preferably arranged at the outer edge of the imaging element. A diffusion receiver arranged in this manner has the advantage that it does not lie in the directed radiation paths and thus, can automatically only be struck by diffusion radiation, wherein a least possible attenuation of the diffusion radiation exists due to the immediate proximity of the diffusion receiver to the imaging element, since the distance of the diffusion receiver to the origin of the diffusion radiation is chosen nearly as small as possible.

In detail, there are a plurality of possibilities for designing and further developing the device according to the invention as will be apparent from the following detailed description of the embodiments in connection with the accompanying drawings.

DETAILED DESCRIPTION OF THE INVENTION

Figure 1:
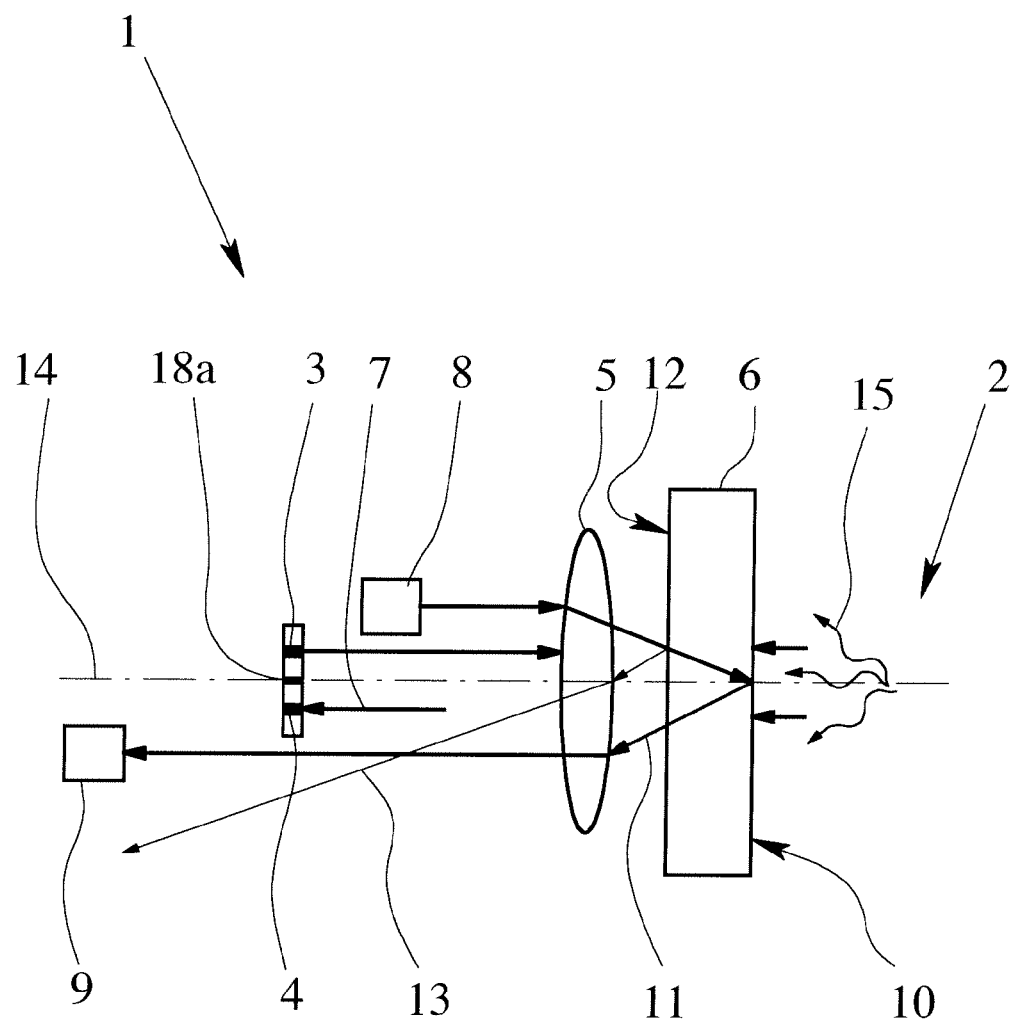
FIG. 1 schematically shows a first embodiment of the device according to the invention for synchronized measurement of diffusion and/or absorption and/or refraction of a sample and FIG. 2 schematically shows a modified version of the embodiment of the device according to FIG. 1.
Figure 2:
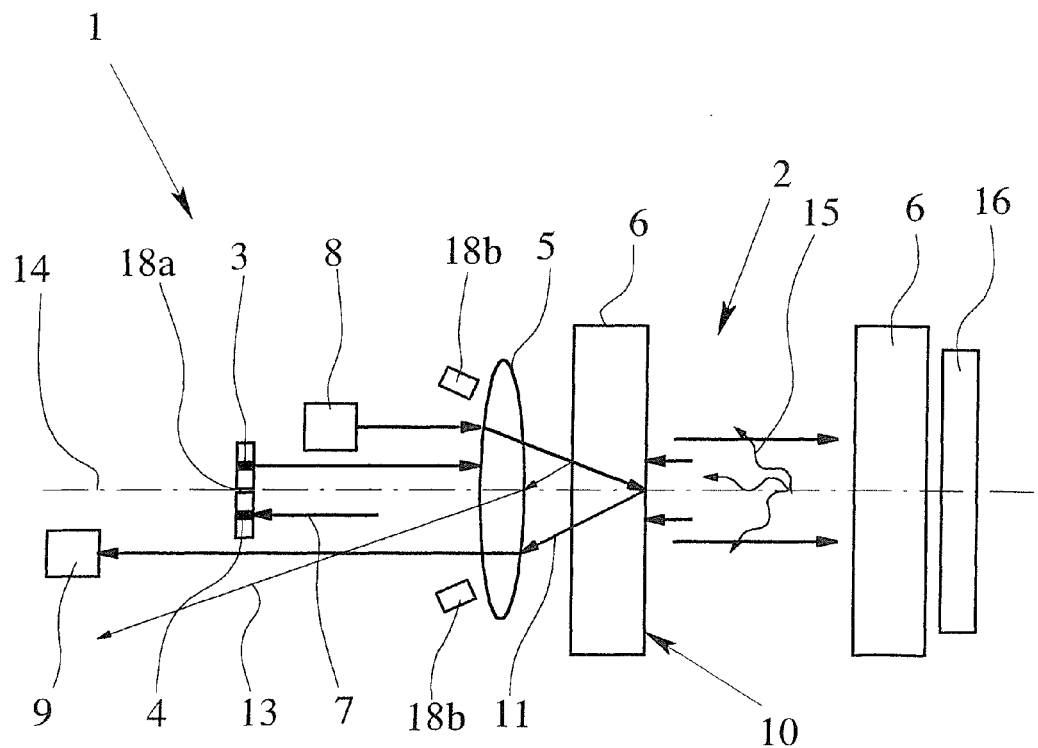

FIGS. 1 & 2 each show an embodiment of a measuring device 1 according to the invention for measuring the diffusion and/or absorption and/or refraction of a sample 2. The device 1 has a radiation source 3, a receiving element 4 an optical imaging element 5 in the form of a lens and a protection element 6. The radiation source 3 and the receiving element 4 are arranged on the sensor side of the optical imaging element 5 and the protection element 6 is arranged on the sample side of the imaging element 5 and neighbors the imaging element 5. The protection element 6 protects the device 1 from the sample 2 penetrating into the sensor side of the device 1, i.e., in the part of the device that also includes the radiation source 3, the receiving element 4 and the optical imaging element 5. The radiation source 3, the imaging device 5 and the receiving element 4 are collectively arranged so that transmitted sample radiation 7 can be received by the receiving element 4.

Furthermore, in the device 1 according to FIGS. 1 & 2, a refraction radiation source 8 and a refraction receiver 9 are arranged on the sensor side of the imaging element 5, and in respect to the imaging element 5, so that the specularly reflected refraction radiation 11 of the sample 2 on the sample side interface 10 of the protection element 6 can essentially be received by the refraction receiver 9 and the specularly reflected radiation 13 on the imaging element side interface 12 of the protection element 6 essentially cannot be received by the refraction receiver 9. This design of the measuring device allows for a strict separation between the specularly reflected refraction radiation 11 on the sample side interface 10 of the protection element 6 and the specularly reflected radiation 13 on the imaging element side of the protection element 6, since only the specularly reflected refraction radiation 11 of the sample 2 on the sample side interface 10 of the protection element 6 can be applied to the refraction receiver 9 and is only struck by this radiation in the operating mode. The devices 1 of the invention are advantageous in that an antireflective coating of the protection element 11, in particular an antireflective coating on the imaging element side interface 12 of the protection element 6 is not necessary, which is advantageous in terms of costs.

In the illustrated embodiments, the distance of the refraction radiation source 8 from the optical axis 14 of the imaging element 5 is greater than the distance of the radiation source 3 from the optical axis 14 of the imaging element 5 and the distance of the refraction receiver 9 from the optical axis 14 of the imaging element 5 is greater than the distance of the receiving element 4 from the optical axis 14 of the imaging element 5. It is thus achieved that the radiation path of the refraction radiation 11 emitted by the refraction radiation source 8 and specularly reflected on the sample side interface 10 of the protection element 6 takes course largely outside of the radiation path of the sample radiation 7 emitted by the radiation source 3 and transmitted through the sample 2, so that the refraction receiver 9, in particular, is not struck by the transmitted sample radiation 7.

In the illustrated embodiments, it is also advantageous that the refraction radiation source 8 is arranged between the radiation source 3 and the imaging element 5, i.e., it is relatively close to the sample 2 with correspondingly higher attainable radiation intensity in the sample 2. It is also advantageous that the refraction receiver 9 is further away from the imaging element 5 than the receiving element 4. It is thus achieved that diffusion radiation 15 of the sample 2 also possibly striking the refraction receiver 9 has only a very low intensity, since the undirected diffusion radiation 15 diminishes with the square of the distance from its origin.

A device 1 is shown in FIG. 2, in which a mirror 16 is arranged on the sample side of the imaging element 5 so that the radiation emitted from the radiation source 3 passes through a transparent sample 2 and strikes the receiving element 4—after reflection of the radiation on the mirror 16. Such an arrangement has the advantage that the transmitted radiation can be created on the side with the sensor, which allows for a possible housing of the device 1 (not shown here) to be compactly built.

In the illustrated embodiments, the refraction radiation source 8 emits radiation at at least one defined wavelength, wherein the refraction receiver 9 is particularly sensitive to radiation from the refraction radiation source 8, which, in the shown embodiments, is implemented by an optical filter that is not shown in detail. Due to this measure, the signal-to-noise ratio of the specularly reflected radiation 13 from the imaging element side interface 12 of the protection element 6 to the diffusion radiation 15 can be additionally improved.

Further, it is shown in FIGS. 1 & 2 that, in the device 1, at least one diffusion receiver 18a, 18b is provided and arranged in such a manner that the diffusion receiver 18a, 18b can essentially be struck by the diffusion radiation 15 of the sample 2 and the diffusion receiver 18a, 18b is, in particular, essentially cannot be struck by the specularly reflected refraction radiation 11 of the sample 2. It is thus possible to evaluate the amount of diffusion radiation 15 that strikes not only the diffusion receiver 18, 18b, but also the receiving element 4, or, respectively, the refraction receiver 9.

The illustrated embodiments of the device 1 are further designed so that the diffusion radiation 15 received and identified by the diffusion receiver 18a, 18b is used to compensate the diffusion radiation 15 that can be received by the refraction receiver 9. The term "compensate" is understood here, above all, as a mathematical or, respectively, signal-based correction of the radiation intensity detected by the refraction receiver 9, in particular, a mathematical/signal-based correction using subtraction of a weighted portion of the diffusion radiation 15 received and identified by the diffusion receiver 18a, 18b from the total radiation received by the refraction receiver 9.

It has been shown to be advantageous that the diffusion receiver 18a is arranged close to or on the optical axis 14 of the imaging element 5, wherein, in the shown embodiments, the diffusion receiver 18a is arranged, above all, closer to the optical axis 14 of the imaging element 5 than the radiation source 3 and the receiving element 4. Here, the diffusion receiver 18a is arranged at the same distance from the imaging element 5 as the radiation source 3 and the receiving element 4, i.e., it is also essentially arranged at a distance from the imaging element 5 defined by the focal length of the imaging element 5.

However, it is even more advantageous—as is shown in FIG. 2—to arrange the diffusion receiver 18b on the sensor side of and adjacent to the imaging element 5, wherein the diffusion receiver 18b is directed toward the sample 2 and arranged on the outer edge of the imaging element. Due to the relative closeness of the diffusion receiver 18b to the sample 2, the diffusion radiation 15 is only slightly weakened, at least decidedly less weakened than in the arrangement of the diffusion receiver in the area of the radiation source 3 of the receiving element 4, since the undirected, emitted diffusion radiation 15 diminishes with the square of the distance from its origin and at a location further away from the sample 2, only an essentially lower intensity of the diffusion radiation 15 exists and is, thus, detectable.

What is claimed is:

1. Device for measuring at least one diffusion, absorption and refraction of radiation by a sample, comprising:

a radiation source, at least one receiving element, an optical imaging element, a protection element, open free space being located between the protection element and the optical imaging element, a refraction radiation source arranged between the radiation source and the optical imaging element, and a refraction receiver wherein the radiation source and the receiving element are arranged on a sensor side of the optical imaging element, open free space being located between the optical imaging element and the radiation source and between the optical imaging element and the receiving element, wherein the protection element is arranged on a sample side of the imaging element and adjacent to the imaging element, wherein the radiation source, the imaging element and the receiving element are collectively arranged so that at least one of directly transmitted and specularly reflected sample radiation are receivable by the receiving element, wherein the refraction radiation source and the refraction receiver are arranged on the sensor side of the imaging element and are arranged relative to the imaging element so that refraction radiation of the sample specularly reflected by a sample side interface of the protection element can essentially be received by the refraction receiver, and the radiation specularly reflected by an imaging element side interface of the protection element is essentially prevented from being received by the refraction receiver, open free space being located between the optical imaging element and the refraction radiation source and between the optical imaging element and the refraction receiver, wherein a distance of the refraction radiation source from the optical axis of the imaging element is greater than a distance of the radiation source from the optical axis of the imaging element wherein a mirror is arranged on the sample side of the imaging element so that radiation emitted from the radiation source passes at least partially through a transparent sample, reflects from the mirror, and strikes the receiving element.

2. Device according to claim 1, wherein a distance of the refraction receiver from the optical axis of the imaging element is greater than a distance of the receiving element from the optical axis of the imaging element.

3. Device according to claim 1, wherein a distance of the refraction receiver from the optical axis of the imaging element is greater than a distance of the receiving element from the optical axis of the imaging element.

4. Device according to claim 1, wherein the refraction radiation source emits radiation at at least one defined wavelength, wherein the refraction receiver is particularly sensitive to radiation from the refraction radiation source, and wherein the refraction receiver has an optical filter.

5. Device according to claim 1, wherein at least one diffusion receiver is provided and arranged for being struck by diffusion radiation of the sample and is essentially precluded from being struck by specularly reflected refraction radiation of the sample.

6. Device according to claim 5, wherein for compensating for diffusion radiation received by the refraction receiver, compensation means are provided for subtracting a weighted portion of diffusion radiation received and identified by the diffusion receiver from the radiation received by the refraction receiver.

7. Device according to claim 5, wherein the diffusion receiver is arranged close to or on the optical axis of the imaging element and closer to the optical axis of the imaging element than at least one of the radiation source and the receiving element, and wherein the diffusion receiver is arranged essentially at the same distance from the imaging element as at least one of the radiation source and the receiving element.

8. Device according to claim 5, wherein the diffusion receiver is arranged on the sensor side of and adjacent to the imaging element, and wherein the diffusion receiver is directed toward the sample.

9. Device according to claim 8, wherein the diffusion receiver is arranged on an outer edge of the imaging element.

10. Device for measuring at least one diffusion, absorption and refraction of radiation by a sample, comprising:
a radiation source,
at least one receiving element,
an optical imaging element,
a protection element, open free space being located between the protection element and the optical imaging element,
a refraction radiation source arranged between the radiation source and the optical imaging element, and
a refraction receiver,
wherein the radiation source and the receiving element are arranged on a sensor side of the optical imaging element, open free space being located between the optical imaging element and the radiation source and between the optical imaging element and the receiving element,
wherein the protection element is arranged on a sample side of the imaging element and adjacent to the imaging element,
wherein the radiation source, the imaging element and the receiving element are collectively arranged so that specularly reflected sample radiation is receivable by the receiving element,
wherein the refraction radiation source and the refraction receiver are arranged on the sensor side of the imaging element and are arranged relative to the imaging element so that refraction radiation of the sample specularly reflected by a sample side interface of the protection element can essentially be received by the refraction receiver, and the radiation specularly reflected by an imaging element side interface of the protection element is essentially prevented from being received by the refraction receiver, open free space being located between the optical imaging element and the refraction radiation source and between the optical imaging element and the refraction receiver,
wherein a distance of the refraction radiation source from the optical axis of the imaging element is greater than a distance of the radiation source from the optical axis of the imaging element.

11. Device according to claim 10, wherein a mirror is arranged on the sample side of the imaging element so that radiation emitted from the radiation source passes at least partially through a transparent sample, reflects from the mirror, and strikes the receiving element, and
wherein the radiation source, the imaging element and the receiving element are collectively arranged so that at least one of directly transmitted and specularly reflected sample radiation are receivable by the receiving element.

12. Device, for measuring at least one diffusion, absorption and refraction of radiation by a sample, comprising:
a radiation source,
at least one receiving element,
an optical imaging element,
a protection element,
a refraction radiation source, and
a refraction receiver,
wherein the radiation source and the receiving element are arranged on a sensor side of the optical imaging element,
wherein the protection element is arranged on a sample side of the imaging element and adjacent to the imaging element,
wherein the radiation source, the imaging element and the receiving element are collectively arranged so that specularly reflected sample radiation is receivable by the receiving element,
wherein the refraction radiation source and the refraction receiver are arranged on the sensor side of the imaging element and are arranged relative to the imaging element so that refraction radiation of the sample specularly reflected by a sample side interface of the protection element can essentially be received b the refraction receiver and the radiation specularly reflected by an imaging element side interface of the protection element is essentially prevented from being received by the refraction receiver wherein a distance of the refraction radiation source from the optical axis of the imaging element is greater than a distance of the radiation source from the optical axis of the imaging element, and wherein at least one diffusion receiver is provided and arranged for being struck by diffusion radiation of the sample and is essentially precluded from being struck by specularly reflected refraction radiation of the sample.

13. Device according to claim 12, wherein for compensating for diffusion radiation received by the refraction receiver, compensation means are provided for subtracting a weighted portion of diffusion radiation received and identified by the diffusion receiver from the radiation received by the refraction receiver.

14. Device according to claim 12, wherein the diffusion receiver is arranged close to or on the optical axis of the imaging element and closer to the optical axis of the imaging element than at least one of the radiation source and the receiving element, and wherein the diffusion receiver is arranged essentially at the same distance from the imaging element as at least one of the radiation source and the receiving element.

15. Device according to claim 12, wherein the diffusion receiver is arranged on the sensor side of and adjacent to the imaging element, and wherein the diffusion receiver is directed toward the sample.

16. Device according to claim 15, wherein the diffusion receiver is arranged on an outer edge of the imaging element.

17. Device for measuring at least one diffusion, absorption and refraction of radiation by a sample, comprising:
a radiation source,
at least one receiving element,
an optical imaging element,
a protection element, open free space being located between the protection element and the optical imaging element,
a refraction radiation source, and
a refraction receiver, the refraction receiver being further away from the optical imaging element than the at least one receiving element,
wherein the radiation source and the receiving element are arranged on a sensor side of the optical imaging element, open free space being located between the optical imaging element and the radiation source and between the optical imaging element and the receiving element,
wherein the protection element is arranged on a sample side of the imaging element and adjacent to the imaging element,
wherein the radiation source, the imaging element and the receiving element are collectively arranged so that specularly reflected sample radiation is receivable by the receiving element,
wherein the refraction radiation source and the refraction receiver are arranged on the sensor side of the imaging element and are arranged relative to the imaging element so that refraction radiation of the sample specularly reflected by a sample side interface of the protection element can essentially be received by the refraction receiver, and the radiation specularly reflected by an imaging element side interface of the protection element is essentially prevented from being received by the refraction receiver, open free space being located between the optical imaging element and the refraction radiation source and between the optical imaging element and the refraction receiver, wherein a distance of the refraction radiation source from the optical axis of the imaging element is greater than a distance of the radiation source from the optical axis of the imaging element, and wherein a minor is arranged on the sample side of the imaging element so that radiation emitted from the radiation source passes at least partially through a transparent sample, reflects from the mirror, and strikes the receiving element.

18. Device for measuring at least one diffusion, absorption and refraction of radiation by a sample, comprising:
a radiation source,
at least one receiving element,
an optical imaging element,
a protection element, open free space being located between the protection element and the optical imaging element,
a refraction radiation source arranged between the radiation source and the optical imaging element, and
a refraction receiver, the refraction receiver being further away from the optical imaging element than the at least one receiving element,
wherein the radiation source and the receiving element are arranged on a sensor side of the optical imaging element, open free space being located between the optical imaging element and the radiation source and between the optical imaging element and the receiving element,
wherein the protection element is arranged on a sample side of the imaging element and adjacent to the imaging element,
wherein the radiation source, the imaging element and the receiving element are collectively arranged so that specularly reflected sample radiation is receivable by the receiving element,
wherein the refraction radiation source and the refraction receiver are arranged on the sensor side of the imaging element and are arranged relative to the imaging element so that refraction radiation of the sample specularly reflected by a sample side interface of the protection element can essentially be received by the refraction receiver, and the radiation specularly reflected by an imaging element side interface of the protection element is essentially prevented from being received by the refraction receiver, open free space being located between the optical imaging element and the refraction radiation source and between the optical imaging element and the refraction receiver,
wherein a distance of the refraction radiation source from the optical axis of the imaging element is greater than a distance of the radiation source from the optical axis of the imaging element.

* * * * *